US011241147B2

(12) United States Patent
Hayut et al.

(10) Patent No.: US 11,241,147 B2
(45) Date of Patent: Feb. 8, 2022

(54) GUIDED ENDOTRACHEAL INTUBATION SYSTEM

(71) Applicants: Yissum Research Development Company of the Hebrew University of Jerusalem Ltd., Jerusalem (IL); Hadasit Medical Research Services and Development Ltd., Jerusalem (IL)

(72) Inventors: Itai Hayut, Tel Aviv (IL); Elchanan Fried, Jerusalem (IL); Yaakov Nahmias, Rishon Le Zion (IL); Tommy Weiss-Sadan, Jerusalem (IL); Ariel Shrem, Jerusalem (IL)

(73) Assignees: Yissum Research Development Company of the Hebrew University of Jerusalem Ltd., Jerusalem (IL); Hadasit Medical Research Services and Development Ltd., Jerusalem (IL)

( * ) Notice: Subject to any disclaimer, the term of this patent is extended or adjusted under 35 U.S.C. 154(b) by 1139 days.

(21) Appl. No.: 14/891,611

(22) PCT Filed: May 16, 2014

(86) PCT No.: PCT/IL2014/050428
§ 371 (c)(1),
(2) Date: Nov. 16, 2015

(87) PCT Pub. No.: WO2014/184796
PCT Pub. Date: Nov. 20, 2014

(65) Prior Publication Data
US 2016/0227991 A1 Aug. 11, 2016

Related U.S. Application Data

(60) Provisional application No. 61/950,413, filed on Mar. 10, 2014, provisional application No. 61/824,015, filed on May 16, 2013.

(51) Int. Cl.
*A61B 1/06* (2006.01)
*A61B 1/00* (2006.01)
(Continued)

(52) U.S. Cl.
CPC ............ *A61B 1/06* (2013.01); *A61B 1/00009* (2013.01); *A61B 1/04* (2013.01); *A61B 1/0661* (2013.01);
(Continued)

(58) Field of Classification Search
CPC ....... A61B 1/106; A61B 1/0009; A61B 1/267; A61M 16/04; A61M 16/0465
See application file for complete search history.

(56) References Cited

U.S. PATENT DOCUMENTS 5,560,351 A * 10/1996 Gravenstein ...... A61M 16/0488
128/200.26
6,096,066 A * 8/2000 Chen ...................... A61N 5/062
607/88
(Continued)

*Primary Examiner* — LaToya M Louis
(74) *Attorney, Agent, or Firm* — Greenberg Traurig, LLP

(57) ABSTRACT

A guided tracheal intubation system using an autonomous modulated light source, outputting modulated illumination at a constant level, and externally applied to the subject's larynx region. An optical imaging system receives a video stream from within the subject's throat, including modulated illumination from the subject's trachea. A display control system performs signal processing on the modulated content of the images, and outputs frames of those images in which the intensity level of illumination from the trachea can be controlled without any need to change the illumination output from the modulated light source. The light source has no connection with the rest of the system, and need contain no more than a battery, a power supply circuit and a light source. It can therefore be of low cost and can be made disposable, such as in the form of an adhesive patch applied to the subject's neck.

17 Claims, 5 Drawing Sheets

(51) Int. Cl.
 *A61B 1/267* (2006.01)
 *A61M 16/04* (2006.01)
 *A61B 1/04* (2006.01)

(52) U.S. Cl.
 CPC ......... *A61B 1/267* (2013.01); *A61M 16/0488* (2013.01)

(56) References Cited

U.S. PATENT DOCUMENTS

| | | | |
|---|---|---|---|
| 8,574,152 B2 * | 11/2013 | Czaniera | A61B 1/267 600/109 |
| 2007/0129603 A1 * | 6/2007 | Hirsh | A61B 1/00048 600/120 |
| 2011/0178369 A1 * | 7/2011 | Qiu | A61B 5/0084 600/109 |
| 2014/0058253 A1 * | 2/2014 | Prough | A61B 5/0095 600/424 |
| 2014/0186791 A1 * | 7/2014 | Lovely | A61B 5/0088 433/29 |

* cited by examiner

GUIDED ENDOTRACHEAL INTUBATION SYSTEM

FIELD OF THE INVENTION

The present invention relates to the field of endotracheal intubation, especially using external illumination to assist in the positioning of the endotracheal tube in the trachea of the subject.

BACKGROUND OF THE INVENTION

Endotracheal intubation is a well-known and widely used practice performed when normal ventilation of the patient's lungs may be impaired. Failure to artificially ventilate an apneic patient rapidly could result in serious brain damage or death. During patient intubation, a flexible tube, also known as an endotracheal tube, is used. A distal end of the tube is placed within the patient's trachea. The proximal end of the tube can be attached to a resuscitator bag or any other device, supporting the respiratory process. During patient intubation, there is a risk of accidental misplacement of the endotracheal tube into the esophagus. This condition can in itself cause death and disability if not quickly detected. When performing tracheal intubation, a common method is to use an imaging device usually in the form of a fiber-optic endoscope or using a device that consists of a rigid body with a camera in its distal end. Both classes of devices provide an image of the patient's vocal folds and the glottis, in order to facilitate tracheal intubation. However, when using internally illuminated endoscopic images, it is often difficult for the user to identify the exact trachea location in order to ensure performing the intubation properly, especially in trauma cases, where blood and secretions may be present, and where speed may be vital. A number of prior art publications suggest the use of illumination applied externally to the neck of the patient, in the region of the vocal cords, so that the preferentially illuminated trachea becomes prominently visible, and thus easier to target by the user, or by an automatic homing device for the endotracheal tube.

In U.S. Pat. No. 6,161,537 to D. Gravenstein et al, for "Transtracheal Energy Application and Sensing System for Intubation: Method and Apparatus", there is described such a system. In order to accommodate differences in transmission of the external illumination into the glottal region of the patient's throat, the external light source is controlled by means of electronic feedback circuitry connected to and driven by the detected signal processing system, for providing an auto-gain feature. This thus involves the use of a controllable level illumination source for the tracheal identification, concomitant control circuitry and a feedback link from the user signal processing and viewing module to the externally applied tracheal identification illumination.

In US Patent Application Publication No. US 2011/0178369, for "System and Method for Intubation" to C. Cui, there is described an automatic endotracheal tube intubation system and method, using an external trachea identifier source, which can be a light source, disposed on the patient. However, nowhere in this reference is there mentioned any provision for controlling the intensity level of the external trachea identifier source, which is likely to be necessary to enable efficient and positive video identification of the correct insertion into the trachea.

There therefore exists a need for an endotracheal tube placement and monitoring system, which is convenient to use and of low cost, and which overcomes at least some of the disadvantages of prior art systems and methods.

The disclosures of each of the publications mentioned in this section and in other sections of the specification are hereby incorporated by reference, each in its entirety.

SUMMARY

The present disclosure describes new exemplary systems for the simple yet accurate viewing, guidance and execution of endotracheal intubation. The system utilizes a self-powered, stand-alone external illumination source, supplying a fixed output level of modulated illumination, applied externally to the region of the neck of the subject immediately external to the larynx region. The illumination source can be constructed in the form of a patch applied externally to the patient's throat region, and, because of its simple low-cost manufacture, could be a disposable component for single-event use with the instrument. This illumination is detected by an imaging system which receives its input from an endotracheal placement device, which can either have a detector array at its distal end, or can transmit the imaged view fiber-optically to a detector array disposed in the electronic sensing and control unit. The externally generated illumination is modulated, most conveniently by amplitude modulation, to enable the perceived or apparent imaged level to be adjusted by signal processing of the illumination detected internally within the subject's throat, and to enable effective discrimination and control of the external illumination penetrating into the trachea, as perceived by the sensing and control system, from the internal illumination provided by the endotracheal tube. The discrimination and level control can be achieved by using phase manipulation of the modulated illumination sensed, without the need for any inputs to the external illumination source at all, which itself provides a constant predetermined modulated output level of illumination.

This system enables the user to adjust the level of apparent tracheal illumination seen in the endoscopic images generated, the term apparent being used to emphasize that the actual tracheal illumination emitted from the trachea is constant (provided that the external illumination source is not moved, and that the patient does not move) and the different illumination level perceived is achieved by signal processing performed on the received image data. This system also enables the control system to use this perceived image data of the trachea to effectively perform automatic illumination level control, and automatic or semi-automatic steering of the endotracheal tube towards the trachea entrance, using images or image data having predetermined illumination and contrast characteristics.

The system enables the maintenance of the apparent imaged intensity of the light received from the external source at a level optimized for the detection of the trachea. If the level is too weak, the trachea may not be positively detectable, and if it is too strong, illumination may be collected from both the trachea and the esophagus, or light may be reflected or scattering from the surrounding tissues, thereby causing anatomical identification errors. Furthermore, as the location of the distal end of the endotracheal tube changes as it is advanced down the throat towards the vocal cords, or even into the trachea, the distance to the light source changes significantly, and the level of detected external illumination also changes.

Control of these changes is achieved in the present described systems without the need for any feedback mechanism that adjusts the intensity of the light source itself, which can be an autonomous element, unconnected electronically or wirelessly to the sensing and display control system. The image intensity control is performed entirely by signal processing within the sensing and display unit, increasing or decreasing the modulated light component of the image so that its apparent intensity remains optimal, before displaying it to the user, or before using it for a task such as intubation tube guidance.

The modulated illumination emitted by the external source should advantageously be at a wavelength which is readily transmitted through the tissues of the throat, such that it penetrates without undue attenuation, and also which has good detection sensitivity by commonly used photosensors, such as silicon-based CCD or CMOS arrays. Therefore, it is to be understood that use of the terms "light" or "illumination" in this disclosure is not intended to be limited to the visible region, but is understood to include any wavelength region which can thuswise be used by the system. Additionally, the modulation frequency should be commensurate with the frame frequency of readily available and standard video imaging devices, thereby keeping the system simple and of low cost.

Furthermore, although the system has been generally described in this disclosure, in terms of a video image display system, this being a commonly used output for visually facilitating endotracheal intubation, it is to be understood that the apparatus and methods of this disclosure can equally well be used in order to provide image data output for use in generating automatic gain control for the images or parts of the images to be generated, or in order to provide data for automatic guidance of the intubation tube during insertion.

Additionally, for an immobile patient and firmly affixed external light source, the modulated illumination level which penetrates the trachea and is then detected as being emitted from the trachea, has an effectively constant level. Therefore, it is to be understood that references made to the sensed or perceived or apparent illumination level, or similar language, are intended to refer to the output of the control and display system after signal processing of the image data, to enhance or amend the content of the true illumination detected. This is applicable whether the image is in a true displayed image form, or as image data for use in control tasks. Such terms are also to be thuswise understood when claimed.

There is thus provided in accordance with an exemplary implementation of the devices described in this disclosure, a system for performing guided tracheal intubation on a subject, comprising,
(i) an autonomous light source, providing a substantially constant level modulated illumination output, adapted to be externally applied to the neck of the subject in the region of the subject's larynx,
(ii) an optical sensing system receiving a stream of image data from an endotracheal placement device within the throat of the subject, the optical image data including data relating to the level of the modulated illumination which has penetrated the trachea of the subject, and
(iii) a control system adapted to perform signal processing on modulated content of the received stream of image data, and to generate image output data which enables the apparent sensed level of illumination from the trachea to be adjusted.

In such a system, the autonomous light source is unconnected to the control system by wire or wirelessly. Additionally, the signal processing may utilize phase manipulation of the optical image data, in order to discriminate between the modulated illumination which has penetrated the trachea of the subject, and illumination applied internally to the subject's larynx region from the endotracheal placement device. Furthermore, the apparent sensed level of illumination from the trachea may be adjusted by a user of the system during the guided tracheal intubation. Alternatively or additionally, the apparent sensed level of illumination from the trachea may be adjusted automatically to provide a predetermined level of contrast in images generated from the image data.

In further exemplary implementations of the above mentioned systems, the autonomous modulated light source may comprise at least one battery, at least one light emitter, and a circuit for powering the at least one light emitter. In this implementation, the at least one light emitter may be a light emitting diode. In any of the previously mentioned systems, the illumination may have a wavelength within the range of from 0.4 micrometers to 1.4 micrometers.

In yet other implementations, the autonomous modulated light source may comprise either an adhesive element or a strap, for application to the neck of the subject in the region of the subject's larynx. The autonomous modulated light source may also be adapted to be disposable after a single use.

Another example implementation involves a patch adapted to be externally applied to the neck of a subject, comprising:
(i) at least one battery,
(ii) at least one light emitter, and
(iii) an electronic circuit for powering the at least one light emitter such that it emits modulated illumination,
wherein the patch is adapted to penetrate the modulated illumination into the trachea of the subject such that an optical sensing system associated with an endotracheal placement device within the throat of the subject, can detect that part of the modulated illumination penetrating the trachea.

In such an implementation, the patch need have no functional connection with the optical sensing system by wire or wirelessly. Additionally, the modulated illumination may be emitted at a substantially constant power level. The patch may most conveniently be disposable.

There is further provided yet other implementations describing a method of performing guided tracheal intubation on a subject, comprising,
(i) externally illuminating the neck of the subject in the region of the subject's larynx with an autonomous light source providing a substantially constant level, modulated illumination output,
(ii) inserting an endotracheal placement device into the throat of the subject,
(ii) optically sensing a stream of optical image data received from an endotracheal placement device inserting into the throat of the subject, the optical image data including data relating to the level of the modulated illumination which has penetrated the trachea of the subject, and
(iii) performing signal processing on modulated content of the received stream of image data to generate image output data which enables the apparent sensed or perceived level of illumination from the trachea to be adjusted.

In such a method, the sensed level of illumination from the trachea may be adjusted without any connection to the autonomous light source by wire or wirelessly. Additionally, the signal processing may utilize phase manipulation of the optical image data, in order to discriminate between the modulated illumination which has penetrated the trachea of the subject, and illumination applied internally to the subject's larynx region from the endotracheal placement device. Furthermore, the apparent sensed or perceived level of illumination from the trachea may be adjusted by a user of the system during the guided tracheal intubation. Alternatively or additionally, the apparent sensed level of illumination from the trachea may be adjusted automatically to provide a predetermined level of contrast in images generated from the image data.

According to further exemplary methods, any of the above mentioned methods may be performed with the autonomous modulated light source comprising at least one battery, at least one light emitter, and a circuit for powering the at least one light emitter. In that case, the at least one light emitter may be a light emitting diode. In any of these methods, the illumination may have a wavelength within the range of from 0.4 micrometers to 1.4 micrometers.

In yet further implementations, the autonomous modulated light source may be applied to the neck of the subject by use of an adhesive element or a strap. Additionally, the autonomous modulated light source may be disposed after a single use.

In any of the above described systems and methods, the sampled image data may need to be obtained at a frequency at least twice as high as the frequency of the modulated illumination output. Furthermore, the modulated illumination output may be square wave or sinusoidally modulated. Finally, in any of the above described embodiments, the stream of image data may conveniently be a video stream of images.

BRIEF DESCRIPTION OF THE DRAWINGS

The present invention will be understood and appreciated more fully from the following detailed description, taken in conjunction with the drawings in which:

FIG. 4A illustrates schematically a novel intubation illumination system of the present disclosure, while

DETAILED DESCRIPTION

Figure 1:
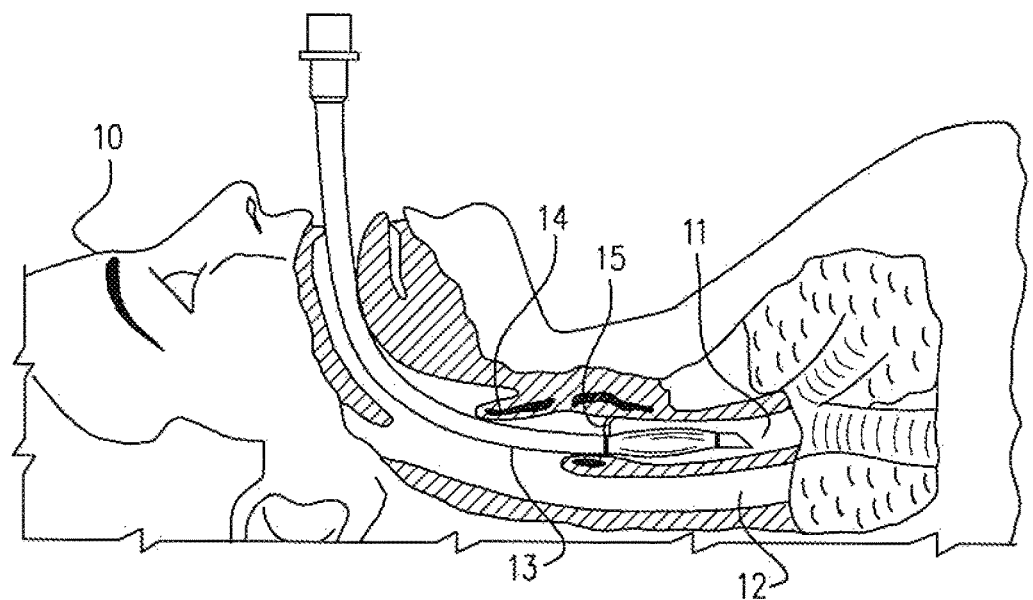
FIG. 1 shows schematically a conventional endotracheal procedure being performed on a patient.

Reference is now made to FIG. 1, which illustrates schematically a conventional endotracheal procedure being performed on a patient 10. The trachea 11 is shown in its location in front of the esophagus 12, and an endotracheal intubation tube 13 has been successfully inserted past the epiglottis 14 and past the vocal chords 15 which are located at the junction of the trachea 11 and the esophagus 12, into the trachea. The problem of successfully negotiating the junction of the trachea and the esophagus is clear from FIG. 1. In commonly used procedures, the attending personnel manipulate the intubation tube into its correct position in the trachea by endoscopically viewing the progress of the distal tip of the intubation tube using illumination conveyed internally down the intubation tube assembly.

Figure 2:
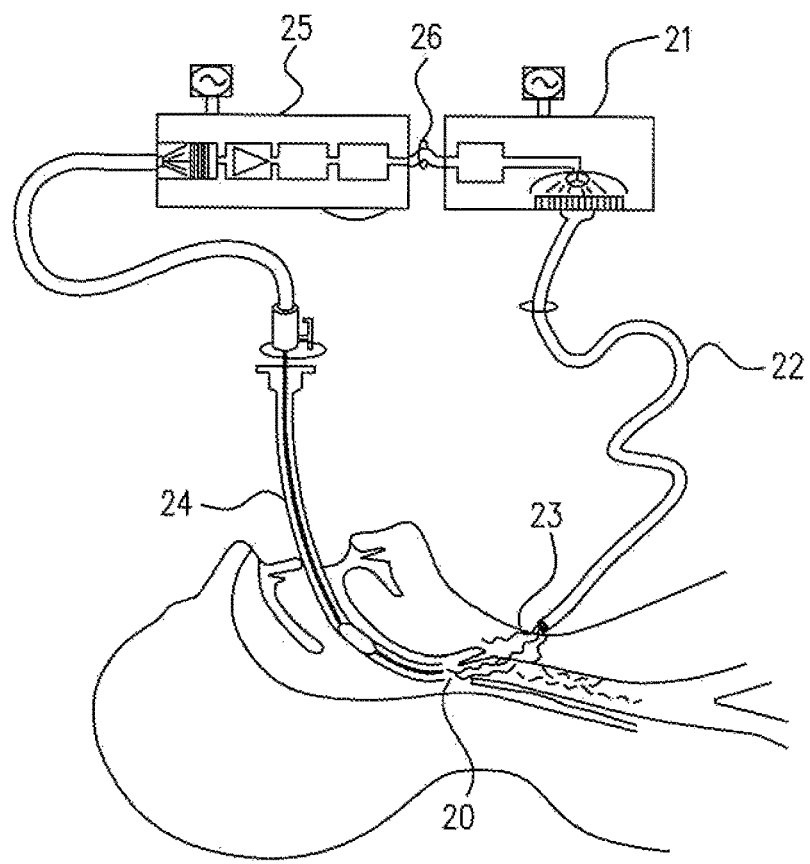
FIG. 2 is a schematic view of a prior art sensing system for tracheal intubation, making use of an externally applied illumination source.

Reference is now made to FIG. 2, which is a schematic view of a prior art sensing system for tracheal intubation, as described in the above mentioned U.S. Pat. No. 5,560,351 to Gravenstein et al. In this system, an energy source 21, which is conveniently an optical source, conveys illumination down a light guide 22 to the external region 23 of the patient's throat, and the light passing through the tissue of the patient's throat illuminates the trachea far more strongly than the esophagus. An endoscopic intubation tube 24 provides an image of the junction region, which is viewed in the display and processing, and steering system 25. Because of the increased illumination in the trachea, the display signal processing software can determine the position of the entrance to the trachea, and can selectively enable the intubation tube to be directed into the trachea.

However, as in all such tracheal imaging systems, there exists the problem that the illumination sensed internally within the patient's throat region, can vary considerably because any cross-sectional population of patients will have a variety of neck sizes and skin colors. These will range from the small, thin, baby's neck, which has very little light absorption ability and therefore will have a very high intra-airway intensity level, to the thick neck of, for instance, an overweight, adult patient, where the illumination penetrating to the larynx region and hence to the image sensor, will be substantially lower. The illuminating device and power level used for the baby would be almost useless for performing the procedure on the large adult patient. In order to overcome this problem, the system described in U.S. Pat. No. 5,560,351 has a light intensity auto-gaining feature, in which a feedback loop is established between the level of light detected by the endoscopic intubation tube sensor electronic circuitry, and the light level applied from the light source unit to the outside of the patient's throat. As indicated in U.S. Pat. No. 5,560,351, in order to influence light source power, the electronic circuitry 25 and the light source unit 21 must be electronically linked, as shown by the electronic communication cable connection 26 in FIG. 2.

A further need for controlled adjustment of the illumination level in such a system is because of the change in sensed illumination as the intubation tube is moved down the patient's throat. In order to maintain a reasonable level of sensed illumination from the externally located source, and also in order to effectively discriminate the sensed illumination from the external source from any illumination internally provided by the illumination system of the intubation tube endoscope, the externally emitted illumination should be changed to compensate for changes in the optical transmission through the neck cartilage and tissue to the viewing lens of the endoscope, as it moves down the throat.

Figure 3:
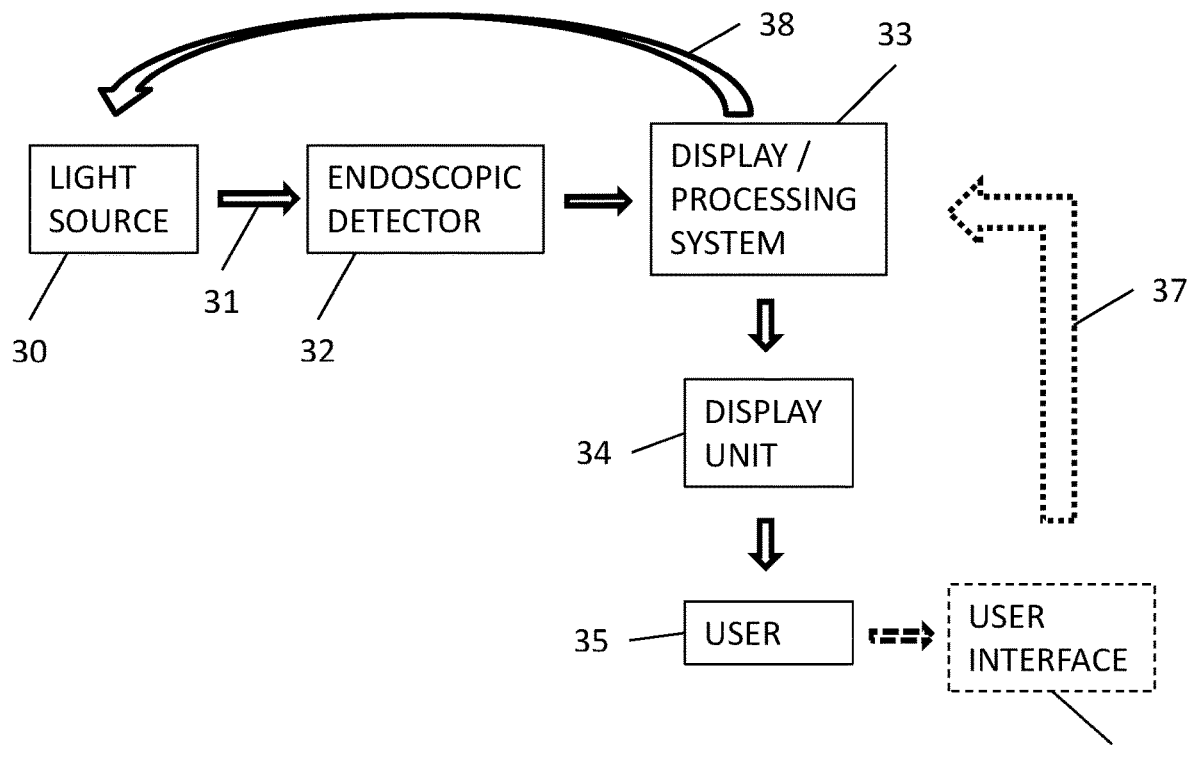
FIG. 3 schematically shows the system architecture of the prior art intubation system shown in FIG. 2.

Reference is now made to FIG. 3, which schematically shows the system architecture of the prior art intubation system of the type shown in FIG. 2. The externally applied light source 30 delivers its illumination through the patient's tissues, as indicated by the arrow 31, to the region of the trachea/esophagus bifurcation. The endoscopic detector 32 of the endotracheal intubation tube images the inside of the patient's throat, and conveys these images, which could be in the form of a video stream, to the electronic display and processing system 33, which can include display and signal processing hardware and software, for outputting such a video stream to a display unit 34 for view by the user 35. In addition, this electronic unit can include a user interface 36, by means of which the user can control the display function by inputting 37 commands back to the electronic system. After processing the received image intensities, and any user inputs from, the user interface, the electronic system 33, is programmed to send a feedback signal 38 to the light source 30, in order to control the level of the external illumination applied to the patient's throat. The system is thus complex, requiring the use of its own dedicated sensing and illumination units, connected electronically so that they will operate correctly together.

Figure 4A:
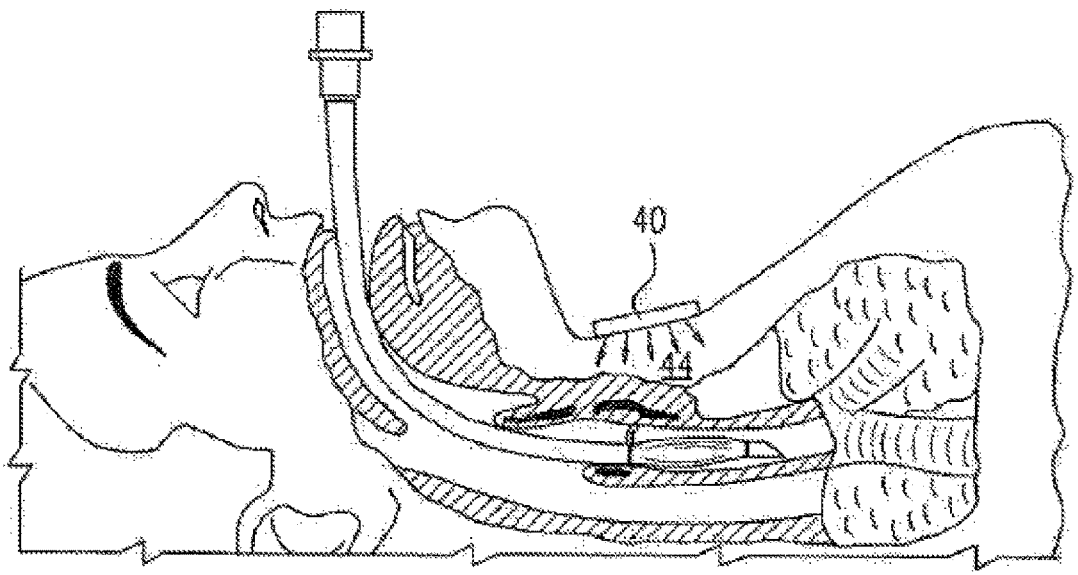

Reference is now made to FIG. 4A, which illustrates schematically an exemplary implementation of the novel intubation illumination system of the present disclosure. The present system differs from that shown in the above mentioned prior art, in that the illumination is supplied by a battery powered, stand-alone light source unit 40, which can most conveniently be in the form of a patch, applied adhesively to the external throat region of the patient opposite the trachea/esophagus bifurcation, such that the illumination 44 emitted by the patch, is directed internally towards the patient's airway. The illumination patch can be held in position either by an adhesive sticky pad, or by means of a strap, or by any other means which will hold the source in position on the patient's throat. The patch can be simply constructed, containing in its simplest implementation, no more than a battery, an illumination source such as one or more LED's, and a power supply for providing the current for the LED's. Because of this simple and low cost structure, the patch can be manufactured to be disposable, such that its use becomes extremely simple. The patch may be applied to the patient's throat, and once the intubation has been completed, it can be removed and discarded. For such a disposable illumination patch, a battery of low capacity may be used, capable of supplying power to the light source only for the duration of one intubation procedure, or somewhat more for safety considerations. The illumination patch is adapted to emit a constant level of average light output, and can thus be completely independent of any input signals from other electronic control units. The wavelength of the illumination 44 emitted by the light source 40 can conveniently be in the range of the visible to near infra-red, which is a range which has good transmission through the tissues of the patient's neck, and to which silicon photo-detector arrays, whether CCD or CMOS, have good sensitivity. Such Si camera arrays are preferable because of their low cost and wide availability. The VIS-NIR wavelengths most typically used for implementing the systems of the present disclosure, range from approximately 0.4 to 1.4 µm, though wavelengths outside of this range may also be possible.

Figure 4B:
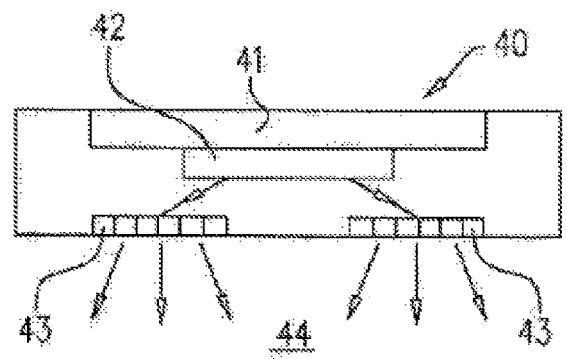
FIG. 4B is a schematic drawing of an exemplary disposable illumination patch for use in the system of FIG. 4A.

FIG. 4B is a schematic drawing of an exemplary embodiment of such a disposable illumination patch 40, showing the battery 41, electronic circuitry 42 for generating the modulated drive current for the illumination source, and an illumination source, in this case shown as arrays of light emitting diodes 43, emitting their illumination 44. Although for the purposes of showing its internal construction, the disposable illumination patch 40 of FIG. 4B is shown as a planar unit, it is to be understood that it is most conveniently constructed of a flexible material, so that it can conform to the profile of the patient's neck region to which it is applied, and be wrapped around that profile. The patches may also be supplied in a range of sizes and output power, to more readily match the physical size and physiology of different patients.

However, regardless of suitability of the size of the patch used, in order for the system to be able to handle the different internally collected levels of airway illumination that could arise from application of an external illumination source having a fixed intensity output level, the imaging module must be able to process and display the internal view of the patient's glottal region at an intensity that can be comfortably viewed by the medical personnel administering the intubation, or readily used by any automatic guidance procedures that require a processable image for implementation of the procedure. Therefore, the imaging module should have a system by which the level of light of the imaged frames of the patient's airways can be controlled. However, in order not to depart from the primary concept of the use of a disposable low-cost illumination patch, the imaging module should operate completely independently from the patch, and have no connection thereto. In order to achieve this, in an exemplary implementation of such an intensity control system, the patch is constructed to emit modulated illumination, at a predetermined modulation rate, and the detection system is adapted to detect the modulated illumination penetrating to the patient's airway, and to adjust the level of the output image for display and processing by phase manipulation and/or gating of the received modulated signal.

Figure 5:
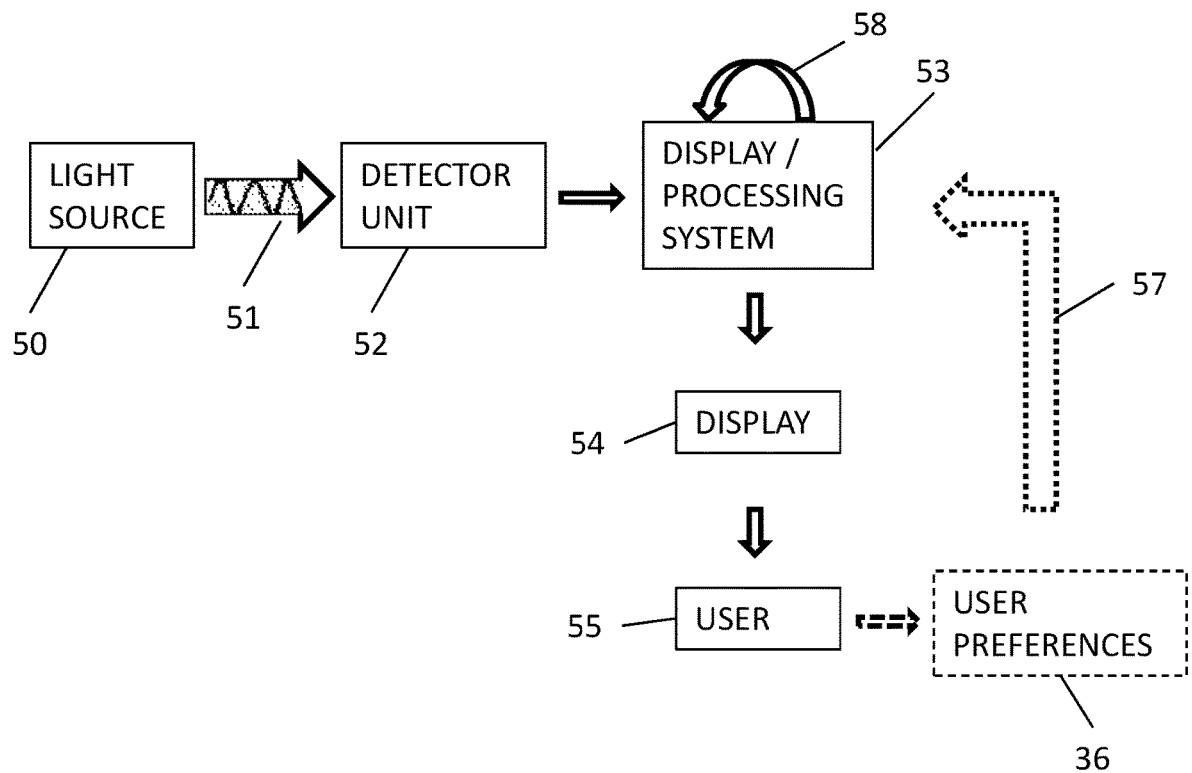
FIG. 5 schematically shows the system architecture of the intubation system of FIG. 4A.

Reference is now made to FIG. 5, which schematically shows the system architecture of the intubation system of the present application, displayed in a similar manner to that shown in FIG. 3 for prior art systems. The externally applied light source 50 is a battery powered passive light source, which can conveniently be disposable after use. The light output 51 is modulated, passes into the patient's glottal region, and is imaged by a detector unit 52, which transfers the video stream to the electronic display and processing system 53. The system differs from that shown in FIG. 3, in that there is no feedback or connection from the electronic display and processing system 53 to the externally applied light source 50. Adjustment 58 of the displayed light intensity is generated either by an auto-gain feedback system within the electronic display and processing system 53, or by user preferences 56, applied by the user 55 as he/she views the images of the intubation on the display 54 as the intubation proceeds. Adjustment of the apparent illumination level, as seen as the displayed light intensity, is achieved entirely within the processing system 53, as indicated by the arrow 58. The user can thus control the intensity of that part of the image arising from the externally applied illumination during the intubation procedure to the level desired for maximum clarity, without communicating either physically or wirelessly with the external battery powered passive light source, which remains completely independent of the detection, control and display electronic units.

An important difference from the prior art systems is that in the system of the present disclosure, the applied external light source 50 transmits a predetermined and fixed light level, which is modulated in order to be able to perform the intensity manipulation of the displayed images, and is completely independent and unconnected to the electronic display and processing system 53. This is one of the features that enables the external light source 50 to be made as a low-cost and disposable item.

The detection and image processing system may function by applying known image processing techniques to separate those parts of the images of the video frames arising from the modulated illumination coming from the external source, from those parts of the images of the video frames arising from the internally applied illumination coming from the endotracheal tube illumination system. By this means it becomes possible to control the comparative level of these two illumination components, and in particular to maintain the modulated illumination emerging from the trachea at a level which enables ready identification of the trachea. In addition to providing the user with a simpler and more readily controllable image display for use in manually guided intubation procedures, this technique may also enable possible automatic guidance of the endotracheal tube into the trachea, with minimal or no user assistance.

One such common image processing technique uses a Fast Fourier Transform (FFT) algorithm to extract any components of the original images detected at the modulation frequency, and to create from these components, a separate image of the modulated illumination, which can then be used as emphasized features overlaid on the conventional for the imaged frames detected by the endotracheal tube video display system. Such an algorithm requires knowledge of the modulation frequency of the externally applied illumination source, but since the standard video frame rates are low, typically no more than a few tens of Hz, modulation frequencies of between 0.5 Hz and 60 Hz can be typically used in this situation. The bandwidth of any FFT algorithm can therefore readily accommodate such a low frequency, and the pre-determined modulation frequency can be closely tracked. Furthermore, the FFT algorithm is sufficiently fast to enable signal processing to the performed in real-time on each frame of the video stream. Eulerian video magnification can be used as another method of delineating the time varying components of the sensed illumination arising from the externally applied modulated light from the constant or slowly varying background illumination from inside the patient's throat regions.

Other possible methods of processing the image data are based on identifying the phase of the modulation in the images and to separate the image into its two component parts—one that is in-phase with the external light source, where light originated from the external light source will be seen with maximal intensity, and one which is out-of-phase with the external light source, where light originated from the external light source will be seen with minimal intensity or will not be seen at all. Another method based on phase manipulation, is to subtract images generated when the externally modulated light source is at its maximal or ON intensity from the images generated when the externally modulated light source is at its minimal or OFF intensity state.

In order to illustrate how these latter two image processing methods operate, reference is now made respectively to FIGS. 6A to 6G and to FIGS. 7A to 7E, which are time based graphs of the sensed illumination, I, displayed by the endoscopic viewing system, as a function of elapsed time, t. The graphs of 6A-6G and 7A-7E are drawn using square-wave pulse modulation, since it is simpler to expound the procedure thus, but it is to be understood that any form of modulation, such as sinusoidal modulation, can equally well be used. The modulation period of the external illumination generated by the throat patch is given by T, and the detected illumination intensity from the internal illumination, is designated by the letter i, while that arising from the external illumination is designated by the letter e. The time graphs illustrate two different ways of controlling the imaged intensity, either for display to the user or for use as an input to any other control feature such as automatic guidance, without the need for any connection, physical or wireless to the throat patch in order to change the apparent illumination level emitted from the throat patch, as displayed or analyzed by the system.

Figure 6A:
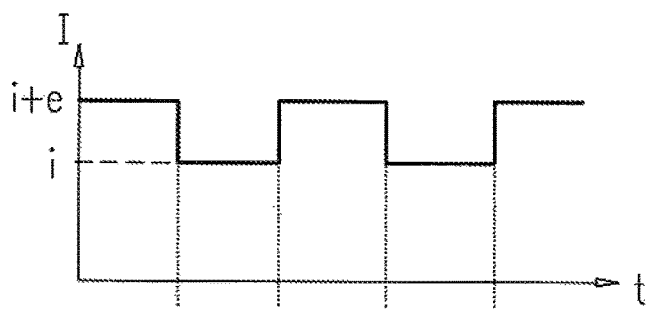
FIGS. 6A-6G illustrate the use of phase sensitive detection techniques on received modulation pulse trains for a method of viewing endoscopic intubation and for controlling the displayed image intensity, using the system of FIG. 4.
Figure 6B:
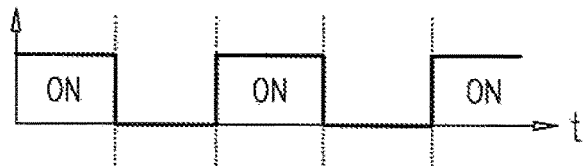
Figure 6C:
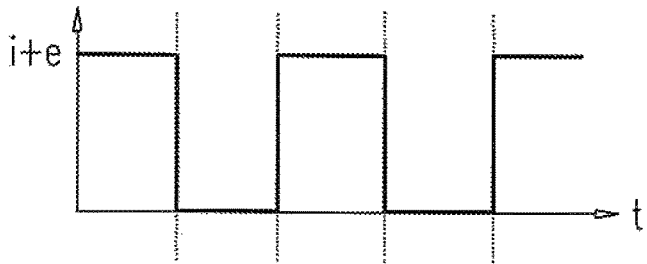

Reference is first made to FIGS. 6A to 6G, which illustrate a method based on phase sensitive detection techniques. FIG. 6A shows the combined output of the internal and external illumination detected by the image sensor. The total illumination is composed of the modulated external illumination e riding on top of the constant internal illumination i. FIG. 6B shows the time trace of a periodic sampling gate applied to the detected illumination of FIG. 6A, the gate temporal profile having the same frequency $f=1/T$ as the external modulated illumination, and being in phase with it. It is to be understood that this sampling process can be performed either by means of a sampling gate implemented in the imaging hardware, or by means of a virtual sampling gate implemented by the image processing algorithms operating on the imaging data. Additionally, although according to the Nyquist sampling theory, in order to accurately detect an unknown modulated light signal, it is necessary to sample it at a frequency at least twice the modulation frequency, if the modulation frequency is known, either by knowledge of the predetermined characteristics of the external illumination source, or if not, by a preliminary calibration step (which does then need to use the Nyquist criterion), this requirement is unnecessary, and only the gating mechanism for selection of the sampled signals at the modulation frequency is considered to explain this method. The method by which phase synchronization is achieved, when the external modulation is free-running and has no electronic connection with the display system, is described hereinbelow. The resulting signal output from the sampling profile shown in FIG. 6B is shown in FIG. 6C, where a signal is shown representing the total illumination i+e, and in phase with the external modulation of the patch source.

Figure 6D:
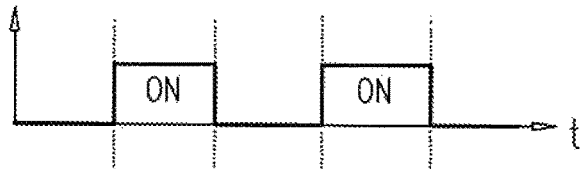
Figure 6E:
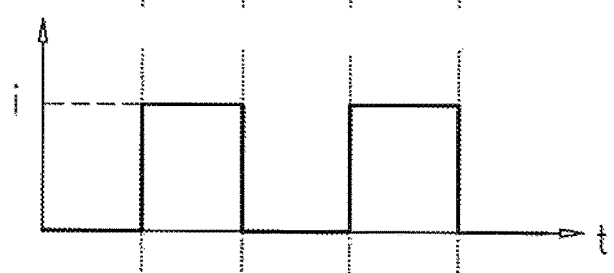
Figure 6F:
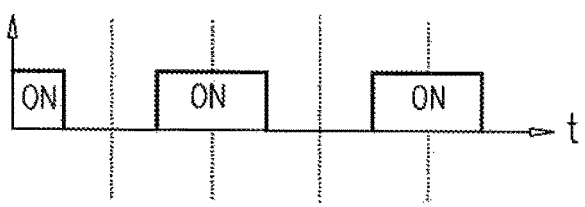
Figure 6G:
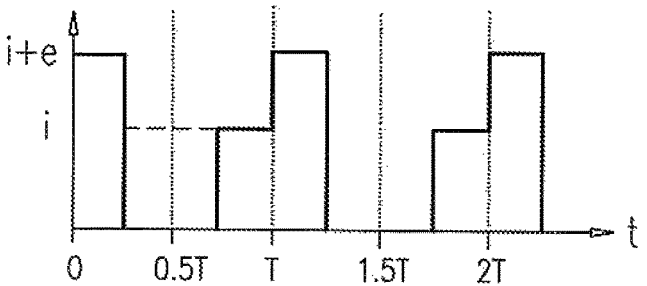

Reference is now made to FIG. 6D, which shows the time trace of the periodic sampling gate of FIG. 6B, but this time with the sampling gate in anti-phase with the external modulated illumination. The resulting signal output is shown in FIG. 6E, where it is seen that since the sampling gate is OFF during the ON periods of the external illumination, the external illumination is completely suppressed, and only the internal illumination, i, is displayed. Thus, by adjusting the phase of the sampling gate relative to the phase of the external modulation illumination, it is possible to adjust the level of the external illumination sensed by the display system. Thus, for instance, in FIG. 6F, the sampling gate is temporally positioned, such that it is 90° out of phase with the externally applied modulation illumination, and the result is intermediate between full suppression and full display of the external illumination, as shown in FIG. 6G.

In order to implement such a phase sensitive detection mode, it is necessary for the display system to be able to synchronize to the phase of the external modulation illumination, which, being generated in a completely independent unit, cannot be measured by direct electronic connection to the source modulation driver. Such synchronization can be achieved by simply varying the phase delay $\tau$ of the sampling gate, while observing the total intensity of the video stream images detected. When the total intensity is at a maximum, that is a sign that the sampling gate timing is exactly in phase with the external modulation.

Figure 7A:
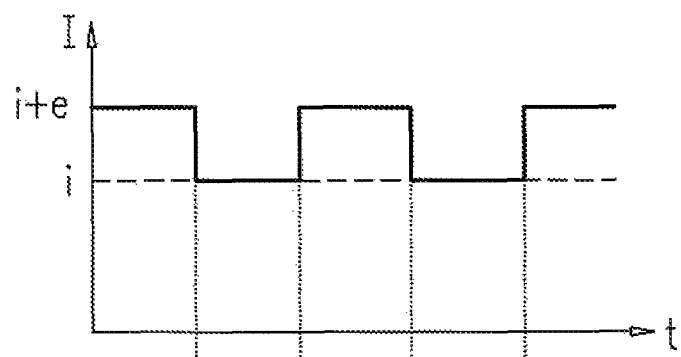
FIGS. 7A-7E illustrate an alternative method to that of FIGS. 6A-6G, in such a manner that the external intensity can be rendered to be the major or even the only component shown in the display system.
Figure 7B:
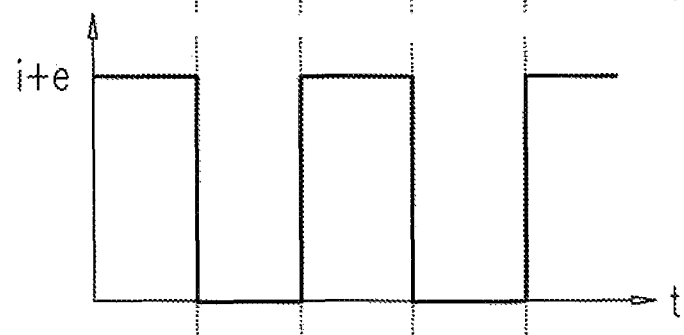
Figure 7C:
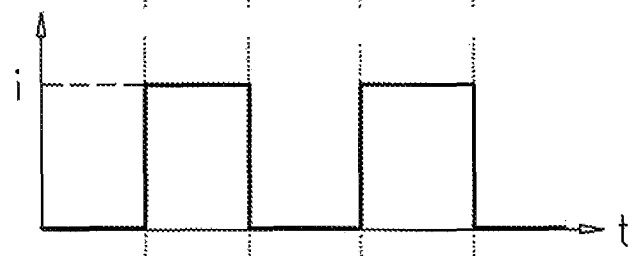
Figure 7D:
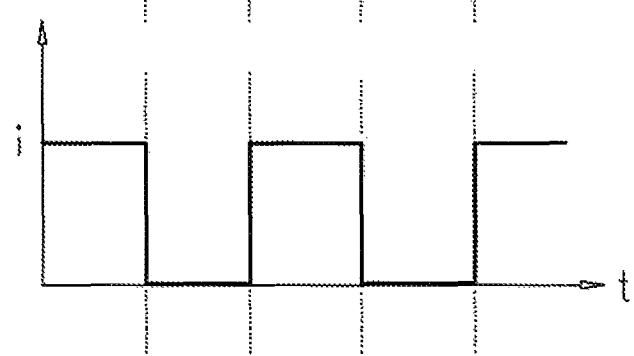
Figure 7E:
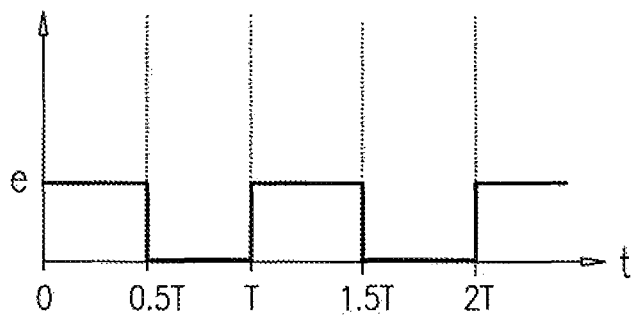

One of the disadvantages of the phase sensitive detection method shown in FIGS. 6A to 6G is that it is impossible to eliminate the effect of the internally generated illumination from the endoscopic source, though of course it is possible to reduce the level of that illumination if necessary. Reference is therefore now made to FIGS. 7A to 7E, which illustrate an alternative method of controlling the displayed image intensity, in such a manner that the external intensity can be rendered to be the major or even the only component shown in the display system. This method operates by use of video frame manipulation, including addition or subtraction of frame sequences. FIG. 7A is equivalent to FIG. 6A, and shows the combined output of the internal and external illumination detected by the image sensor system. FIG. 7B is equivalent to FIG. 6C, and shows the displayed output for in-phase detection of the illumination. FIG. 7C is equivalent to FIG. 6E, and shows the display outputted for anti-phase detection of the illumination, which corresponds to the internal illumination, i, only. The image video frame streams can now be time manipulated by the system algorithm, in order to achieve the desired output. Thus, in FIG. 7D, the internal illumination signal of FIG. 7C has been shifted by 180°, so that it is now in the same phase as the in-phase detected illumination shown in FIG. 6B. If the signal train of FIG. 7D is now subtracted from that of FIG. 7B, the resulting output shown in FIG. 7E is a video train, representing the external illumination only. By varying the phase shift applied to the video train of FIG. 7D, before subtraction from that of FIG. 7B, it becomes possible to vary the comparative percentages of the internal and external illumination shown in the displayed images. Alternatively, attenuation can be applied to either the internal video data stream, as represented by FIG. 7D, or the external video data stream, as represented by FIG. 7E, in order to achieve the optimum illumination combination for the intubation procedure. If an auto gain feature is provided in the display control, then any of these attenuation or phase adjustments can be performed automatically, to provide a loop closing illumination level.

Using the intubation guidance system described in FIGS. 5 to 7E, it is possible readily to implement an automatic intubating system, using the enhanced image of the modulated illumination emitted from the position of the trachea as the target for the endotracheal tube. In such a system, the image is processed in order to isolate or increase the modulated light originated from the external source, and to separate it from the "background" noise which did not originate from the modulated external source. The processing of the image can be done by using the system and algorithms described hereinabove, or by any other methods. In addition, the area in the image where the received intensity of the modulated light is maximal, can be calculated in order to define the preferred direction for the automatic guidance and movement of a mechanical or robotic conduit that carries the intubation tube towards the trachea. In one possible implementation, the tip of the conduit is guided to automatically turn towards the maximum modulated light intensity as calculated by the software, whereas the movement of tip or of the entire conduit forward or backward within the patient's throat may be performed manually by the user. According to a further embodiment, motion of the tip or of the entire conduit forward or backward can also be automatically controlled by the system, so that the endotracheal the tube can be automatically located within the trachea.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

What is claimed is:

1. A system for performing guided tracheal intubation on a subject, comprising:

(1) an autonomous patch, wherein the autonomous patch includes:
　(a) a light source;
　(b) a power source; and
　(c) an electronic controller,
　wherein the electronic controller is coupled to the light source,
　wherein the electronic controller is configured to provide a modulated drive current to the light source so as to operate the light source to provide a substantially constant level predetermined modulated illumination output,
　wherein the predetermined modulated illumination output has a predetermined maximal intensity and is periodically modulated between a maximal intensity state and a minimal intensity state at a predetermined frequency, and
　wherein the autonomous patch is configured to be externally applied to the neck of the subject in the region of the subject's larynx;
(2) an optical sensing system configured to receive a stream of image data from an endotracheal placement device within the throat of the subject, the optical image data including data relating to a level of the predetermined modulated illumination provided by the light source of the autonomous patch which has penetrated the trachea of the subject; and
(3) a control system configured to perform signal processing on the received stream of image data based on the predetermined frequency, and to generate a modified stream of image output data having an adjusted intensity of the predetermined modulated illumination output,
wherein the autonomous patch is not connected to the control system by wire or wirelessly and does not receive a feedback signal from the control system.

2. The system according to claim 1, wherein the signal processing utilizes phase manipulation of the optical image data, in order to discriminate between the modulated illumination which has penetrated the trachea of the subject, and illumination applied internally to the subject's larynx region from the endotracheal placement device.

3. The system according to claim 1, wherein the apparent sensed level of illumination from the trachea is automatically to provide a predetermined level of contrast in images generated from the image data.

4. The system according to claim 1, wherein the illumination has a wavelength within the range of from 0.4 micrometers to 1.4 micrometers.

5. The system according to claim 1, wherein the predetermined modulated illumination output is square wave or sinusoidally modulated.

6. The system according to claim 1, wherein the stream of sampled image data is a video stream of images.

7. The system according to claim 1, wherein the at least one light emitter is a light emitting diode and wherein the modulation frequency is in the range of 0.5 Hz to 60 Hz.

8. The system according to claim 1, wherein the autonomous patch is disposable.

9. A patch adapted to be externally applied to the neck of a subject, wherein the patch comprising comprises:
(1) at least one battery;
(2) at least one light emitter; and
(3) an electronic circuit,
　wherein the electronic circuit is configured to provide a modulated drive current to the at least one light emitter such that the at least one light emitter emits a modulated illumination output, wherein the modulated illumination output has a predetermined maximal intensity and is periodically modulated between a maximal intensity state and a minimal intensity state at a predetermined frequency, wherein the patch is adapted such that the modulated illumination penetrates at least into the trachea of the subject such that an optical sensing system associated with an endotracheal placement device within the throat of the subject can detect that part of the modulated illumination penetrating the trachea, and wherein the patch has no functional connection with the optical sensing system by wire or wirelessly.

10. The patch according to claim 9, wherein the patch is disposable.

11. A method for performing guided tracheal intubation on a subject, comprising:
(1) providing an autonomous patch, wherein the autonomous patch includes:
  (a) a light source;
  (b) a power source; and
  (c) an electronic controller,
  wherein the electronic controller is coupled to the light source,
  wherein the controller is configured to provide a modulated drive current to the light source so as to operate the light source to provide a substantially constant level predetermined modulated illumination output,
  wherein the predetermined modulated illumination output has a predetermined maximal intensity and is periodically modulated between a maximal intensity state and a minimal intensity state at a predetermined frequency, and
  wherein the autonomous patch is configured to be externally applied to a neck of a subject in a region of a larynx of the subject;
(2) applying the autonomous patch to the larynx of the subject;
(3) externally illuminating the neck of the subject in the region of the larynx of the subject with the modulated illumination output provided by the light source of the autonomous patch;
(4) optically sensing a stream of optical image data received from an endotracheal placement device inserted into the throat of the subject, the optical image data including data relating to a level of the predetermined modulated illumination which has penetrated the trachea of the subject; and
(5) performing signal processing on the received stream of image data based on the predetermined frequency to generate a modified stream of image output data having an adjusted intensity of the predetermined modulated illumination output,
wherein the sensed level of illumination from the trachea can be adjusted without any connection to the autonomous light source by wire or wirelessly.

12. The method according to claim 11, wherein the signal processing utilizes phase manipulation of the optical image data, in order to discriminate between the modulated illumination which has penetrated the trachea of the subject, and illumination applied internally to the subject's larynx region from the endotracheal placement device.

13. The method according to claim 11, wherein the apparent sensed level of illumination from the trachea is adjusted automatically to provide a predetermined level of contrast in images generated from the image data.

14. The method according to claim 11, wherein the illumination has a wavelength within the range of from 0.4 micrometers to 1.4 micrometers.

15. The method according to claim 11, wherein the predetermined modulated illumination output is square wave or sinusoidally modulated.

16. The method according to claim 11, wherein the stream of image data is a video stream of images.

17. The method according to claim 11, wherein at least one light emitter is a light emitting diode and wherein the modulation frequency is in the range of 0.5 Hz to 60 Hz.

* * * * *